United States Patent [19]

Slaugh

[11] Patent Number: 5,030,792

[45] Date of Patent: Jul. 9, 1991

[54] PROCESS FOR PREPARING 1-OCTENE

[75] Inventor: Lynn H. Slaugh, Cypress, Tex.

[73] Assignee: Shell Oil Company, Houston, Tex.

[21] Appl. No.: 64,356

[22] Filed: Jun. 22, 1987

[51] Int. Cl.$^5$ ............................................. C07C 1/213
[52] U.S. Cl. .................................... 585/639; 560/244; 560/265; 560/227
[58] Field of Search ............... 560/244, 265, 227, 113, 560/103; 585/639

[56] References Cited

U.S. PATENT DOCUMENTS 3,534,088 10/1970 Bryant et al. ........................ 560/244
3,775,469 11/1973 Jung .................................... 560/244

Primary Examiner—Jose G. Dees

[57] ABSTRACT

This invention relates to a process for producing 1-octenes comprising reacting conjugated dienes and carboxylic acids in the presence of palladium, platinum or ruthenium catalysts to produce 2,7-alkadienyl esters, contacting the 2,7-alkadienyl esters with hydrogen to produce alkyl esters and subsequently pyrolyzing the alkyl esters to produce 1-octene and carboxylic acid.

8 Claims, No Drawings

PROCESS FOR PREPARING 1-OCTENE

FIELD OF THE INVENTION

This invention relates to a process for the production of substituted or unsubstituted 1-octene. More particularly, it relates to the production of conjugated diene dimer carboxylates and their subsequent conversion to the 1-octenes.

SUMMARY OF THE INVENTION

The instant invention relates to a process for producing unsubstituted or lower alkyl substituted 1-octenes. In this process a lower molecular weight conjugated diene is reacted with a carboxylic acid in the presence of a palladium, platinum or a ruthenium catalyst to produce a 2,7-alkadienyl ester, the ester is hydrogenated with hydrogen by contact with a hydrogenation catalyst to produce the corresponding alkyl ester, and the alkyl ester is then pyrolyzed by heating between a temperature of about 350° C. and about 550° C. to produce the product 1-octene and the starting carboxylic acid. The product 1-octene and the carboxylic acid may be separated from the product mix and the carboxylic acid may be recycled. The product 1-octenes are suitable for use as co-monomers in the polymerization of polyethylene to produce unique polymer products.

DETAILED DESCRIPTION OF THE INVENTION

The instant process comprises three basic steps. The first step comprises a combined dimerization esterification process. The second step comprises a hydrogenation process, and the third step comprises a pyrolysis step.

The step of simultaneously dimerizing a conjugated olefin and esterifying it with a carboxylic acid utilizing a Group VIII catalyst is known in the art. U.S. Pat. No. 3,407,224, issued Oct. 27, 1968, and U.S. Pat. No. 3,526,314, issued Feb. 9, 1971, both disclose the preparation of 2,7-alkadienyl esters utilizing Group VIII catalysts. These two references are incorporated by reference herein and made it part of this specification.

The conjugated diene employed as a reactant in the first step of the process of the invention is an alpha, omega-conjugated alkadiene having only hydrogen substituents on the terminal carbon atoms of the four-carbon chain. Dienes that possess non-hydrogen substituents on the internal, i.e., non-terminal, carbon atoms are suitably employed, provided that the internal-carbon atom substituents do not unduly sterically hinder the diene dimerization. A preferred class of diene reactants comprises butadiene having from 0 to 2 internal-carbon methyl substituents. These diene compounds are butadiene, isoprene and 2,3-dimethylbutadiene. Of these, butadiene is particularly preferred.

In general, these diene compounds will have the following general formula:

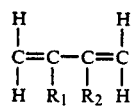

where $R_1$ and $R_2$ are independently hydrogen or alkyl, particularly lower alkyl ($C_3$ or less) or more particularly methyl.

The carboxylic acid employed as a reactant in the first step of the process of the invention contains at least one carboxy group, i.e., a $-CO_2H$ group and may be of complex or of comparatively simple structure. Best results are obtained when a carboxylic acid of relatively simple structure is employed, and a preferred class of organic carboxylic acids comprises carboxylic acids of up to 20 carbon atoms and having from 1 to 4 carboxy groups, preferably 1 to 2 carboxy groups, present within the molecular structure and having no active hydrogen atoms other than that (those) of the carboxy group(s). The organic carboxylic acid reactant is suitably wholly aliphatic in character, wholly aromatic character or incorporates both aliphatic and aromatic moieties; however, the carboxylic acid reactant is free of carbon-carbon unsaturation other than that of any aromatic moieties present within the molecule, that is, the carboxylic acid reactant is free of non-aromatic carbon-carbon unsaturation. Expressed in alternate terms, the carboxylic acid reactant has only aromatic carbon-carbon unsaturation, that is, any carbon-carbon unsaturation present within the reactant molecule is aromatic carbon-carbon unsaturation. The carboxylic acid reactant is a hydrocarbon carboxylic acid containing only atoms of carbon and hydrogen besides the oxygens of the carboxy group(s) present, or is a substituted-hydrocarbon carboxylic acid containing, in addition to atoms of carbon, hydrogen and carboxy oxygen, atoms of halogen, oxygen atoms other than carboxy oxygen atoms, and nitrogen, which additional atoms are present in functional groups such as oxy, keto, carbonyloxy, halo, tertiary amino and like groups. Particularly suited are carboxylic acids of up to 20 carbon atoms, having from 1 to 2 carboxy groups, having no active hydrogen atoms present and being free from non-aromatic carbon-carbon unsaturation selected from hydrocarbon cyclic and acylic carboxylic acids and halohydrocarbon cyclic and acyclic carboxylic acids of up to 4 halogen atoms, hydrocarbon aromatic carboxylic acids and halohydrocarbon aromatic carboxylic acids of up to 4 halogen atoms.

In general, carboxylic acid reactants which are hydrocarbon carboxylic acids as above defined or additionally have present atoms of halogen, are preferred over carboxylic acids with other functional groups. Such carboxylic acid reactants are generically termed (halo)hydrocarbon carboxylic acids, which term refers to carboxylic acids having only atoms of carbon, hydrogen, halogen and carboxylic oxygen. Furthermore, the process of the invention is particularly useful when monocarboxylic acids are employed, particularly hydrocarbon monocarboxylic acids of up to 12 carbon atoms. Particularly preferred are the lower hydrocarbon, particularly alkyl, monocarboxylic acids of up to 3 carbon atoms, most particularly the lower alkyl monocarboxylic acids with up to 3 carbon atoms. Representative preferred acids are acetic acid, propionic acid, butyric and valeric acid.

Illustrative of suitable carboxylic acid reactants are wholly aliphatic carboxylic acids including hydrocarbon aliphatic carboxylic acids, both acyclic and cyclic, such as formic acid, acetic acid, butyric acid, 2-ethylhexanoic acid, dodecanoic acid, glutaric acid, adipic acid, hexadecadioic acid, 2-methylglutaric acid, oxalic acid, cyclopentanecarboxylic acid, tetrahydronaphthalene-1-carboxylic acid, 1,4-dicarboxycyclohexane, 1,2,4,5-tetracarboxycyclohexane, 2-(carboxymethyl)-glutaric acid and 1,4-bis(carboxymethyl)cyclohexane; as well as substituted-hydrocarbon aliphatic carboxylic acids, both acyclic and cyclic, as exemplified by chloroacetic acid, trichloroacetic acid, 3-acetoxypropionic acid, 4-bromocyclohexane-carboxylic acid, N-methyl-piperidine-2-carboxylic acid, 2-ethoxyethanoic acid, 2,2-dichloropropionic acid, 6-dimethylaminohexanoic acid, 4-chloro-3-methoxybutyric acid, 2,3-dichlorobutandioic acid, 3-chloromethylcyclopentane-carboxylic acid, tetrahydropyran-2-carboxylic acid, bis(2-carboxyethyl)ether and 2-trichloromethylsuccinic acid.

Also suitable are carboxylic acid reactants which are wholly aromatic in character, both alicyclic and heterocyclic, as illustrated by hydrocarbon aromatic carboxylic acids such as benzoic acid, terephthalic acid, phthalic acid, naphthalene-1-carboxylic acid, pyromellitic acid, naphthalene-1,4-dicarboxylic acid and the like, as well as wholly aromatic substituted-hydrocarbon carboxylic acids including p-chlorobenzoic acid, pyridine-2-carboxylic acid, m-bromobenzoic acid, 4-chlorophthalic acid, 4,6-dibromonaphthalene-2-carboxylic acid, 2-carboxyquinoline and bis(4-carboxyphenyl)ether.

Carboxylic acids having both aromatic and aliphatic moieties are also suitably employed as reactants in the process of the invention. Such acids are exemplified by hydrocarbon carboxylic acids including phenylacetic acid, p-tert-butylbenzoic acid, m-toluic acid, 2,2-bis(4-carboxyphenyl)propane, tetrahydronaphthalene-2-carboxylic acid, p-octylbenzoic acid, 4-(p-tolyl)butyric acid, 4,4'-dicarboxy-2,2'-diethylphenyl-3,5-dimethyl-benzoic acid and 5-methylisophthalic acid; as well as by substituted-hydrocarbon carboxylic acids, for example, p-trichloromethylbenzoic acid, m-dimethylaminobenzoic acid, 2-(p-chlorophenyl)maleic acid, 3-phenoxypropionic acid, bis(4-carboxyphenylmethyl) ether, p-(benzoyloxy)phenylacetic acid, m-perchloroethylbenzoic acid, 2,3-dibromoterephthalic acid and the like.

The optimum ratio of carboxylic acid reactant to conjugated diene reactant will depend in part upon the functionality of the carboxylic acid reactant, that is, the number of carboxy groups present in the carboxylic acid reactant molecule, as well as the reactant conversion that is desired. Ratios of moles of diene to moles of carboxy group as low as about 1:4 are suitable if only a low conversion is employed. However, to obtain higher conversions, a more substantial proportion of diene is preferred and ratios of moles of diene to moles of carboxy group from 1:1 to about 10:1 are more satisfactory, with best results being obtained when ratios of moles of diene to moles of carboxy group from about 2:1 to about 6:1 are utilized. It should be understood that it is within the contemplated scope of the invention to esterify each carboxy group of the carboxylic acid reactant or only a portion of the total number of carboxy groups. In the latter instance, such restrictive esterification is favored by a molar reactant ratio relatively low in the diene reactant.

The catalyst employed in the first step of the process of the instant invention is a metal compound wherein the metal is selected from palladium, platinum, ruthenium and mixtures thereof. Particularly preferred is palladium.

In one particular modification of the invention, the metal-containing catalyst is introduced as a salt, and palladium, platinum or ruthenium salts of organic or inorganic acids which are strong or weak acids are suitable. Illustrative examples include the halide and oxalate salts. Also suitable are salts wherein the metal is present in the anion as, for example, the use of chloropalladate salt or chloroplatinate salts. Metal complexes may also be suitably used, such as, complexes with tertiary nitrogen-containing ligands. The known $\tau$-allyl complexes are also suitably used.

The catalyst employed in the first step of the process of the invention is a metal compound wherein the metal is selected from palladium, platinum and ruthenium. Particularly preferred as catalyst is a compound of a VIII-C metal having an atomic number from 46 to 78 inclusive, i.e., palladium and platinum. Most preferred as catalyst is a compound of palladium. Without wishing to be bound by any particular theory, it appears that the chemical transformations during the course of the reaction which involve the metal compound are quite complex, probably involving the formation and destruction of complexes between the metal moiety and the diene reactant and/or the presumed diene dimer intermediate. Metal compounds that are soluble in the reaction medium as well as compounds that are superficially insoluble in the reaction system are operable, apparently in the latter case through dissolved metal compound moieties, the formation of which is probably influenced by interaction with the diene reactant and/or the carboxylic acid reactant and the solubilization, resulting therefrom. To obtain optimum reaction rates, the metallic compound is preferably soluble in the reaction mixture or serves as a precursor of a soluble metal compound. It is apparent, however, that the metal-containing catalyst may be employed in any form which serves to introduce the metal compound into the reaction system.

The first step of the process of the invention is characterized by the requirement for only catalytic quantities of platinum, palladium or ruthenium compound. Although utilization of larger amounts of metal-containing catalyst are not detrimental to the process of the invention, amounts larger than about 1% mole based on total reactants are not generally required. Amounts of metal compound less than about 0.001% mole on the same basis are generally unsuitable because of the inevitable physical losses of catalyst during reaction and processing. In general, amounts of catalyst from about 0.01% mole to about 0.5% mole based on total reactants are satisfactory and are preferred. The use of promoters, such as the phenoxide promoter of U.S. Pat. No. 3,407,224 can also be suitable utilized.

The first step of the process of the invention is typically conducted by charging the reactants, catalyst and optional catalyst promoter to an autoclave or similar reactor and maintaining the reaction mixture at reaction temperature until reaction is complete. The method of mixing is not critical. The reaction is suitably conducted throughout a wide range of reaction temperatures and pressures, so long as the reactants are maintained substantially in the liquid phase. Reaction temperatures from about $-20°$ C. to about $150°$ C. are satisfactory, although temperatures from about $0°$ C. to about $130°$ C. are preferred and best results are obtained when a temperature from about $25°$ C. to about $125°$ C. is employed. Typical reaction pressures vary from about 1 atmosphere to about 80 atmospheres. Frequently, good results are obtained when the reaction pressure is autogenous, that is, the pressure generated when the reactants are maintained at reaction temperature in a sealed reaction vessel. Such pressures are from about 1 atmosphere to about 20 atmospheres.

The first step of the process of the invention is conducted in the presence or in the absence of a solvent. In the modification wherein solvent is employed, solvents that are suitable are those capable of dissolving the reactants, catalyst and catalyst promoter, and are inert to the reactants and the products prepared therefrom. Exemplary solvents are ethers, including dialkyl ethers such as diethyl ether, dibutyl ether and methyl hexyl ether; alkyl aryl ethers such as anisole and phenyl butyl ether; cyclic ethers such as tetrahydrofuran, dioxane and dioxolane; and lower alkyl ethers (full) of polyhydric alcohols or polyoxyalkylene glycols such as ethylene glycol dimethyl ether, diethylene glycol dimethyl ether, tetraethylene glycol dimethyl ether and glycol triethyl ether; aromatic hydrocarbons such as benzene, toluene and xylene; N,N-dialkyl alkanoic acid amides, e.g., dimethylformamide and N,N-diethylacetamide; halogenated hydrocarbons such as chloroform, carbon tetrachloride, tetrachloroethylene, methylene chloride and bromoform; sulfoxides such as dimethylsulfoxide; and nitriles such as acetonitrile and benzonitrile. The solvent, if any, is employed in molar excess over the amount of total reactants, and in general, moles of solvent up to 150 moles per mole of total reactants are satisfactory. For convenience, it is generally preferable to conduct the reaction in the absence of added solvent whenever the physical characteristics of the system at reaction temperature, particularly the melting point thereof, will allow. For example, when the process of the invention is employed with a reaction mixture normally liquid at reaction temperature, the process is typically conducted in the absence of solvent. Alternatively, if the reaction mixture is unduly viscous or normally solid at the reaction temperature, solvent is preferably employed to maintain the reactants in the liquid phase.

Subsequent to the first step of the reaction, the reaction mixture may be separated and a desired 1,7-alkadienyl ester is recovered by conventional means such as selective extraction, fractional distillation and chromatographic techniques, which ester is fed to the second step of the instant process. Alternatively, the reaction mixture from the first step may be fed directly to the second step.

The second step of the instant process comprises taking the 2,7-alkadienyl esters of the first step and hydrogenating them by contact with hydrogen and a hydrogenation catalyst to produce the corresponding alkyl esters.

The hydrogenation catalysts utilized in the instant invention can be any of the known hydrogenation catalysts, either heterogeneous or homogeneous catalysts. Typical known hydrogenation catalysts useful in this step of the process comprise the Group VIII metals of the periodic table, i.e., of those containing atomic numbers 26 through 78, particularly those containing atomic numbers 28 through 78. Other known catalysts suitable for hydrogenation in the second step of the instant process include the oxides and sulfides of Group VI, i.e., Cr, Mo and W. The palladium, platinum and ruthenium catalysts utilized the first step of the instant process may also be suitably be utilized in the second step to provide hydrogenation activity. In the latter instance, the catalyst may be from a recycled stream of the first step of the instant process.

The second step of the instant process involves hydrogenation in the presence of hydrogen. The hydrogen may be provided to the reaction mixture in the presence of pure hydrogen or diluted with other gases such as the inert gases or for example, may be present in a process gas such as syngas which is utilized to provide the hydrogen.

The hydrogenation step can be carried out in either a batch process or in a continuous process. In a batch process a homogeneous or heterogeneous catalyst is charged to the reactor along with the reactants and pressured with hydrogen, or a hydrogen-containing gas and allowed to react at the appropriate temperature to hydrogenate the alkyldienyl esters. In a continuous process the catalyst is provided in the form of a packed bed of solid catalyst, preferably supported metal catalyst, and the alkyldienyl ester and hydrogen are simultaneously passed through the bed, which is maintained at reaction conditions.

The hydrogenation step is conducted in the presence or a absence of a solvent. Preferred solvents are those which are inert to the hydrogenation conditions. Exemplary solvents are those noted above as being useful in the first step of the instant process.

The appropriate reaction temperature will vary widely depending on the particular hydrogenation catalyst utilized and its activity. Typical hydrogenation temperatures will range from about 0° C. to about 200° C. Typical hydrogenation pressures will range from about atmospheric to say about 10 bar or higher.

Subsequent to the reaction of this second step of the process, the reaction mixture is separated and the desired alkyl ester product is recovered by conventional means such as selective extraction, fractional distillation and chromatographic techniques. When high activity heterogeneous hydrogenation catalysts and purified 2,7-alkadienyl esters feedstocks are utilized, recovery techniques can be quite simple, involving a simple separation of unreacted gaseous material from the product alkyl esters.

The third step of the instant process comprises taking the alkyl esters of the second step and heating or pyrolyzing them at elevated temperatures to cause a disassociation of the alkyl ester into 1-alkene and carboxylic acid.

The pyrolysis involves passing the alkyl esters through a heated reactor maintained at a temperature ranging from about 350° C. to about 600° C. Preferably the temperature will range from about 400° C. to about 550° C. Pyrolysis reactors are known in the art. Typical examples of suitable pyrolysis reactors that are suitable for use in the third step of the instant process comprise tubular reactors and packed columns. There are no particular pressure limitations on the pyrolysis reaction, and typically the reaction is carried out at about atmospheric pressure. Subsequent to reaction, the reaction mixture is separated into the desired 1-alkene product, unreacted alkyl esters and the regenerated carboxylic acids. The unreacted alkyl esters may be recycled to the start of the third step of the instant process and the regenerated carboxylic acids may be recycled to the first step of the instant process. Depending on pyrolysis conditions, the carboxylic acid anhydride may be produced in addition to the starting carboxylic acid. The anhydride is readily converted by hydrolysis to the acid for recycle.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

In summary, the instant invention comprises a process for producing 1-alkenes of the following general formula:

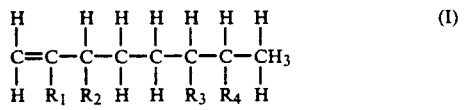

wherein $R_1$, $R_2$, $R_3$ and $R_4$ are independently hydrogen or methyl which process comprises:
a) contacting
  (1) a carboxylic acid of up to 20 carbon atoms, from 1 to 2 carboxy groups, having no active hydrogen atoms not present in carboxyl groups and being free from non-aromatic carbon-carbon unsaturation with
  (2) from about 0.25 mole to about 10 moles per mole of carboxy group of conjugated diene selected from

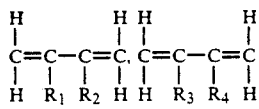

and mixtures thereof
  in the presence of a homogeneous catalyst selected from palladium, platinum and ruthenium at a temperature of from about 20° C. to about 150° C. to produce a 2,7-alkadienyl ester,
b) contacting the 2,7-alkadienyl ester product of step (a) with hydrogen and a hydrogenation catalyst to produce the corresponding alkyl ester, and
c) heating the alkyl ester of step (b) to a temperature between about 350° C. to about 550° C. to produce the corresponding alkene of the general formula I.

The process of the instant invention will be illustrated by the following illustrative embodiment which is provided for illustration and is not intended to limit the scope of the invention.

Illustrative Embodiment

EXAMPLE 1

Step 1: 1,7-alkadienyl ester preparation

To a 300 ml autoclave were added approximately 4.45 mmoles of palladium acetate dissolved in about 40 ml of benzene, and 42 g (0.7 mol) of acetic acid. The reactor was then charged with about 80 g of 1,3-butadiene. The reactor was heated at about 45°–55° C. for about 25 hours, cooled and vented off of 19 liters of gas. The autoclave contents were 104.5 g of colorless liquid product and a black precipitate (spent catalyst). 100 Ml of n-hexane were added to the liquid product and the resultant mixture was extracted with 100 ml of water. This extraction process was repeated utilizing two additional 15 ml portions of water. The remaining organic phase was distilled, separating the hexane from the 1,7-octadienyl ester product.

Step 2: Hydrogenation Process

The 1,7-octadienyl product of step 1 was hydrogenated at 25°–31° C. with 250 psi hydrogen using 0.6 g of 5% palladium supported on barium sulfate. The hydrogenated product was filtered and 29.7 g were recovered. NMR analysis showed the product to be 95% 1-acetoxyoctane and 5% 3-acetoxyoctane.

Step 3: Pyrolysis

30 Ml of the 95% 1-acetoxyoctane and 5% 3-acetoxyoctane product from step 2 was diluted with 60 ml n-heptane and pumped into a Vicor tube at a rate of 8 ml per hr along with 10 ml per minute of nitrogen. Approximately 6 inches of the tube was heated to about 500° C. The product was collected in cold traps. Analysis of the product (excluding n-heptane) gave the following weight percent: $C_3$ and $C_4$ hydrocarbons = 3.3; acetic acid = 22.2; 1-octene = 48 6; internal octenes = 4.6 and the remaining acetoxyoctane = 21.3.

EXAMPLE 2

1,7-Octadienyl trifluoroacetate was prepared by reacting 1 g of palladium acetate in 20 ml of benzene with 102 g of trifluoroacetic acid and 0.96 M butadiene in a 300 ml autoclave at ambient temperature for 4 days.

The resultant 1,7-octadienyl trifluoroacetate was hydrogenated at 150 psig of hydrogen at ambient temperature using 5% palladium on $BaSO_4$ to produce trifluoroacetoxyoctane.

The resultant trifluoroacetoxyoctane was decarboxylated at temperatures ranging from 400°–450° C. to trifluoroacetic acid and product 1-octene. Percent conversions ranged from about 45 to 90%.

I claim:
1. The process of producing 1-alkenes of the following general formula:

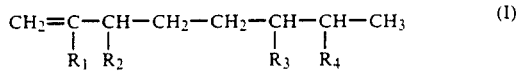

wherein $R_1$, $R_2$, $R_3$ and $R_4$ are independently hydrogen or methyl which process comprises:
  a) contacting
    (1) a carboxylic acid of up to 20 carbon atoms, from 1 to 2 carboxy groups, having no active hydrogen atoms not present in carboxyl groups and being free from non-aromatic carbon-carbon unsaturation with
    (2) from about 0.25 mole to about 10 moles per mole of carboxy group of conjugated diene selected from

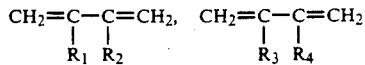

and mixtures thereof, wherein $R_1$, $R_2$, $R_3$ and $R_4$ are independently hydrogen or methyl
    in the presence of a homogeneous catalyst which is a soluble compound of a Group VIII metal compound wherein the metal is palladium, platinum or ruthenium at a temperature of from about 20° C. to about 150° C. to produce a 2,7-alkadienyl ester,
  b) contacting the 2,7-alkadienyl ester product of step (a) with hydrogen and a hydrogenation catalyst to produce the corresponding alkyl ester, and
  c) heating the alkyl ester of step (b) to a temperature between about 350° C. to about 550° C. to produce the corresponding alkene of the general formula I.

2. The process of claim 1 wherein the carboxylic acid is selected from hydrocarbon cyclic and acyclic carboxylic acids and halohydrocarbon cyclic and acyclic carboxylic acids of up to 4 halogen atoms and the conjugted diene is selected from butadiene, isoprene, 2,3-dimethylbutadiene and mixtures thereof.

3. The process of claim 2 wherein the carboxylic acid is an acyclic monocarboxylic acid.

4. The process of claim 1 wherein the carboxylic acid is selected from acetic acid, propionic acid and butyric acid.

5. The process of claim 2 wherein the carboxylic acid is a halo-acyclic monocarboxylic acid.

6. The process of claim 5 wherein the carboxylic acid is trifluoroacetic acid.

7. The process of any of claims 1-6 wherein the conjugated diene is butadiene.

8. The process of any of claims 1 or 2 wherein the carboxylic acid is acetic acid.

* * * * *